United States Patent [19]
Klee et al.

[11] Patent Number: 5,987,959
[45] Date of Patent: Nov. 23, 1999

[54] AUTOMATED RETENTION TIME LOCKING

[75] Inventors: Matthew S. Klee, Wilmington, Del.; Bruce D. Quimby, Lincoln University, Pa.; Leonid M. Blumberg, Hockessin, Del.

[73] Assignee: Hewlett-Packard Company, Palo Alto, Calif.

[21] Appl. No.: 09/036,658

[22] Filed: Mar. 6, 1998

Related U.S. Application Data

[63] Continuation of application No. 08/728,868, Oct. 10, 1996, abandoned.

[51] Int. Cl.$^6$ .................................................. G01N 30/02
[52] U.S. Cl. ........................... 73/1.02; 73/23.22; 73/23.36
[58] Field of Search ............................... 73/23.22, 23.23, 73/23.24, 23.34, 23.36, 1.02, 1.03

[56] References Cited

U.S. PATENT DOCUMENTS

| | | | |
|---|---|---|---|
| 4,927,532 | 5/1990 | Pospisil | 73/23.23 X |
| 5,405,432 | 4/1995 | Snyder et al. | 95/82 |
| 5,436,166 | 7/1995 | Ito et al. | 73/23.36 X |
| 5,670,379 | 9/1997 | Ito et al. | 73/23.22 X |
| 5,827,946 | 10/1998 | Klee et al. | 73/23.36 |

FOREIGN PATENT DOCUMENTS

| | | | |
|---|---|---|---|
| 1-191055 | 8/1989 | Japan | 73/23.23 |

OTHER PUBLICATIONS

HP 5898A Microbial Identification System Operating Manual, Version 3.0 pp. 10–13 & 10–14, P/N 19298–90100, Mar. 1984 (Rev. Oct. 1987).

*Primary Examiner*—Daniel S. Larken
*Attorney, Agent, or Firm*—Richard F. Schuette; Robert C. Sismilich

[57] ABSTRACT

The invention provides a method for automated matching of retention times obtained using a known chromatographic method having a defined set of column parameters and operating parameters to the retention times obtained using a new chromatographic method having a new set of column parameters, wherein the retention times of components separated in accordance with the new chromatographic method are matched to the retention times set forth in the known chromatographic methods. A procedure is described to adjust head pressure to compensate for differences in a new versus the original column, carrier gas, and column outlet pressure of the known method.

23 Claims, 8 Drawing Sheets

REQUIRED PRESSURE CHANGE= (ACTUAL RET. TIME−TARGET RET. TIME)$\frac{\Delta P}{\Delta T}$

AUTOMATED RETENTION TIME LOCKING

This application is a continuation of Ser. No. 08/728,868, filed Oct. 10, 1996, now abandoned.

FIELD OF THE INVENTION

The present invention relates to a method for locking the retention time of compounds in a gas chromatographic analysis such that they match those defined in a known chromatographic method and, more particularly, for adjusting column head pressure to provide for retention time locking so as to eliminate the requirement for the adjustment of calibration and event tables.

BACKGROUND OF THE INVENTION

Figure 1:
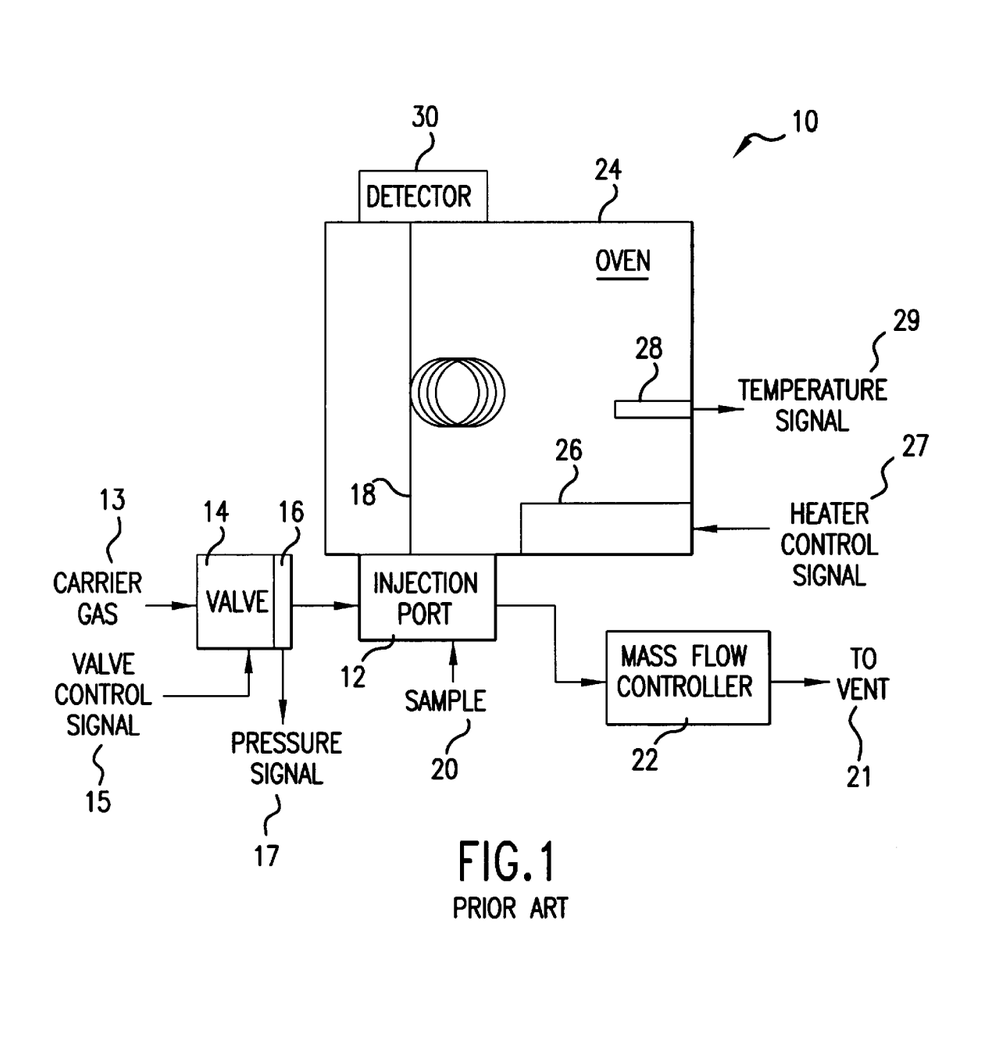
FIG. 1 is an illustration of a prior art gas chromatograph having an integrated pressure programmer.
Figure 2:
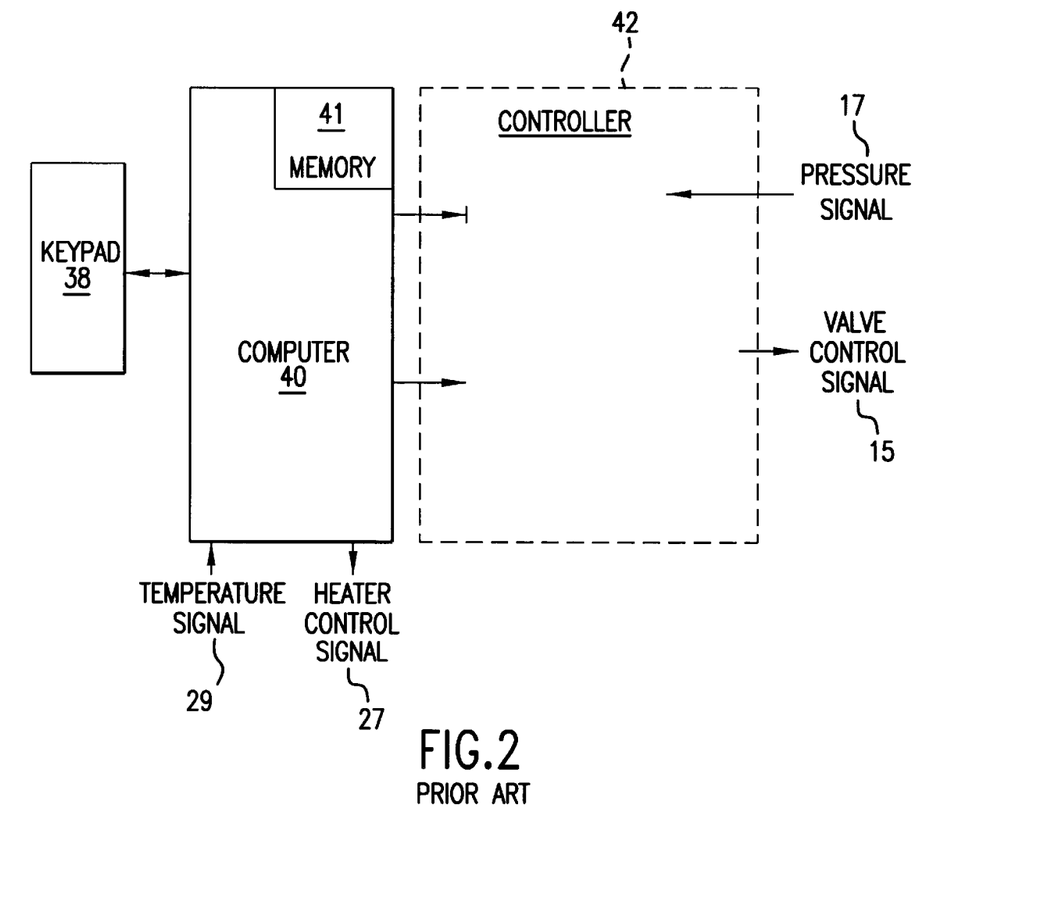
FIG. 2 is a block diagram of the control system of the gas chromatograph in FIG. 1.

A typical gas chromatograph 10 is illustrated in FIG. 1 and includes a column 18 positioned within an oven 24. Chromatographic separation of a sample 20 is accomplished by injecting the sample 20 into a pressurized carrier gas 13 through an injection port 12 into the column 18. Either manual control of pressure valve 14 or electronic pneumatic control provides for adjusting the pressure of the carrier gas 13 at the head of the column 18 (hereinafter "column head pressure") in response to a valve control signal 15. A pressure transducer 16 generates a pressure information signal 17 proportional to the column head pressure; this signal 17 is transmitted to controller 42 (FIG. 2). A heater 26 provides heat to the oven 24 in response to internal control signals (not shown) or to a heater control signal 27 from computer 40. A temperature sensor 28 generates a temperature signal 29 proportional to the temperature in the oven 24; the signal 29 is transmitted to computer 40. The carrier gas/sample combination passing through column 18 is exposed to a temperature profile resulting from the operation of the heater 26 within oven 24. There is a direct correlation between the temperature profile and the retention time of different compounds making up the sample in the column. As compounds elute from the column 18, a detector 30 generates an electrical signal corresponding to some characteristic of the compounds. The non-analyzed portion of the carrier gas/sample combination passes through a mass flow controller 22 to vent 21. FIG. 2 illustrates the electronics employed for controlling the GC, including keypad 38, computer 40, and controller 42. Computer 40 includes a central processing unit, memory 41, and associated devices, such as random access memories, read-only memories, input/output isolation devices, and other components. One of the functions of computer 40 is to control the temperature of oven 24 by monitoring temperature signal 29 from sensor 28 and transmitting the appropriate heater control signal 27 to heater 26. For electronic pneumatic control, one of the functions of controller 42 is to control the column head pressure by monitoring pressure signal 17 from transducer 16 and transmitting the appropriate valve control signal 15 to valve 14.

Figure 3:
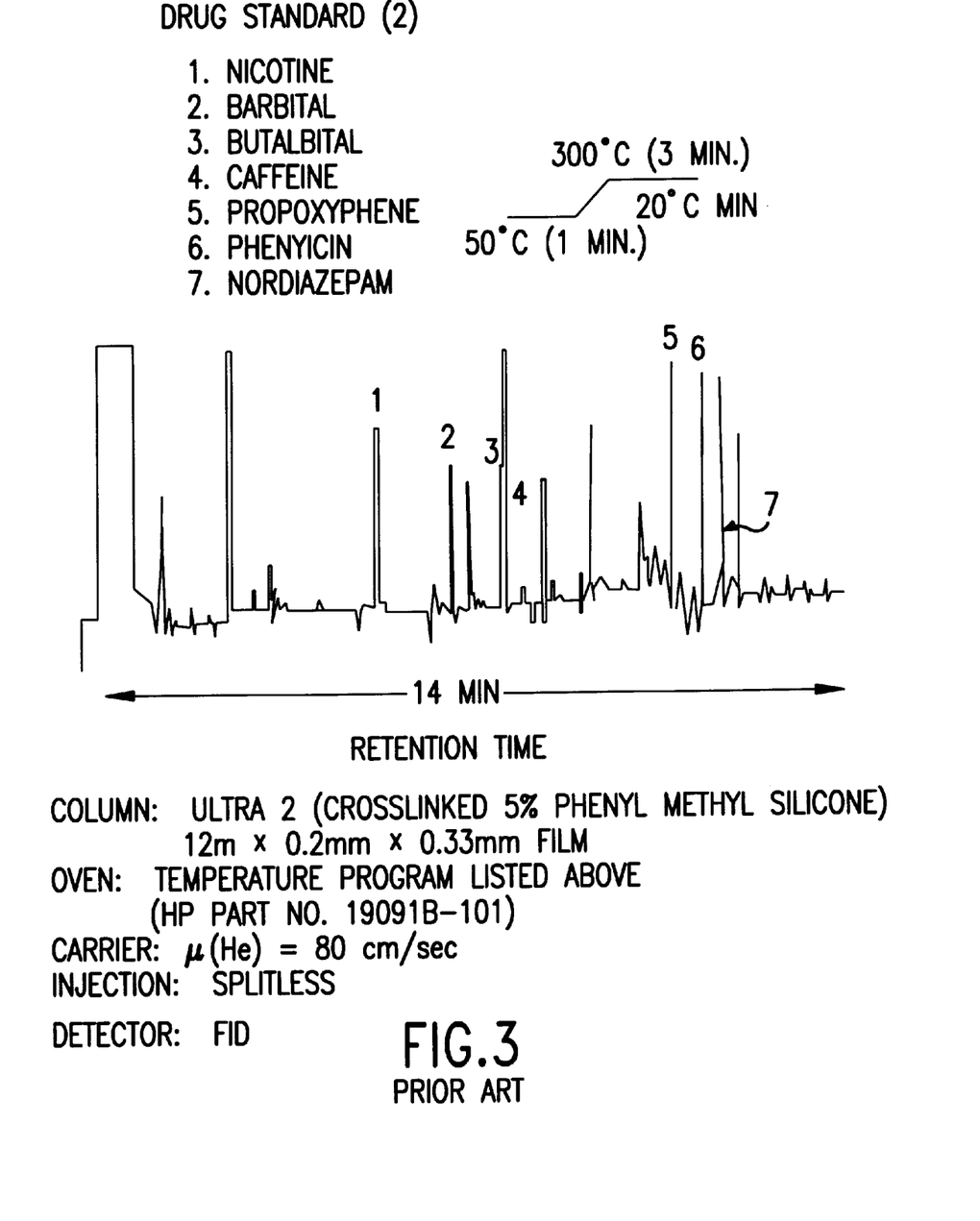
FIG. 3 illustrates the chromatographic output of a known capillary column method entitled "Drug Standard (2)".

Chromatographers spend a significant portion of their time developing and optimizing chromatographic methods for the separation, identification, and quantification of specific compounds within a sample. Such a chromatographic method will specify the use of a column having defined column parameters (e.g., length, stationary phase, and inside diameter) as well as operating parameters for the gas chromatograph (e.g., carrier gas type and pressure, oven temperature, and ramp rates). A compilation of chromatographic methods entitled "Analytical Solutions—a Collection of Chromatograms from Hewlett-Packard" is commercially available from the Hewlett-Packard Company, Palo Alto, Calif. This compilation contains a collection of over 400 capillary column methods developed by Hewlett-Packard field and factory personnel over a period of ten years. FIG. 3 illustrates one such method entitled "Drug Standard (2)" which is employed for identifying drugs and highlights the column parameters and the operating parameters required to replicate this chromatographic method. The column parameters include: column length (l), column inside diameter (id), stationary phase thickness ($d_f$), and stationary phase type). The operating parameters include: carrier gas type, pressure and/or flow rate, and oven temperature (including program ramp rates). A chromatogram highlighting the retention times at which known compounds will elute from the column 18 makes it possible to identify unknown compounds based on the elution order and time.

The chromatographer reviews compilations of chromatographic methods to obtain one having the greatest potential for determining unknown amounts and identities of compounds in samples. However, it is generally not possible to change only one column or operating parameter without affecting the retention time of each compound, resolution, and in many cases, the elution order of each compound. The vast number of column types and nominal sizes makes it quite possible that a chromatographer will be unable to practice a published chromatographic method for lack of a column that matches the column specified in the chromatographic method.

U.S. Pat. No. 5,405,432 entitled "Capillary Column Method Translation" to Snyder et al, and hereby incorporated by reference, teaches a method for translating a known "original" chromatographic method specifying a set of column and operational parameters into a new chromatographic method having possibly new column and/or new operational parameters and a chromatographic output with similar separation. System software running on the gas chromatograph or a remote computer controls a gas chromatograph to automatically reconfigure with the new operational parameters. The existing column and operating parameters are stored such that upon input of the new column parameters, system software has all of the information necessary to perform translation calculations required to obtain the new operating parameters. Once the new operating parameters are calculated, the gas chromatograph is reconfigured such that the chromatographic output of the gas chromatograph with the new column and new operating parameters is substantially the same as with the old column and old operating parameters. However, while elution order may be maintained with this approach, retention times are not locked to those of the original chromatographic method.

A chromatographic method is typically developed with the intent that a chromatographer will be able to practice the method. A problem facing all chromatographers is the inability to exactly replicate column and operating parameters in accordance with a prescribed or translated chromatographic method. Without exact replication, measured retention times do not match the retention times specified in the original chromatographic method or the computerized method files (including calibration and event tables) and can lead to misidentified peaks with grave consequences in drug analysis, enviromental, or petrochemical applications.

Sophisticated integration software (for example, the Hewlett-Packard 3365 ChemStation software available from Hewlett-Packard Company, Palo Alto, Calif.) may be employed, in combination with a preliminary sample injection of a "standard" having known retention times, to update the corresponding calibration table by identifying one or several large and isolated chromatographic peaks as references. However, in order to identify these reference peaks, they must fall within a retention time "reference window". If each reference peak occurs during the window, then the integration software automatically recalibrates to the new retention times by a proportional amount. However, if the retention times of the reference peaks occur outside the reference windows, or if the elution order of any of the standard peaks changes, then the operator must identify patterns of reference peaks and override incorrect peak identifications. While it is possible to broaden or move the reference windows, it can be time consuming and is difficult to automate, especially for the analysis of complex samples having many analytes. Additionally, sufficient broadening of reference windows may cause overlapping windows and misidentification of peaks.

Even assuming that a gas chromatograph has been set up in accordance with a chromatographic method and the retention times of the calibration sample have been calibrated, there exists an ongoing need for recalibration. Deposits of non-volatile compounds at the head of the column which tend to contaminate the column, shift retention times and distort peak shapes necessitating the removal of a portion of the column. The column then exhibits retention times that, under the original operating parameters, are shorter.

There is a need to quickly and easily replicate a method such that it may be used by others without time-consuming calibration and re-calibration upon the modification or replacement of a column without the additional large number of calibration steps required with retention indices. Additionally, it would be advantageous not to require the correction/adjustment of runtime tables (integration, timed events etc.)

It would be advantageous to adjust the operating parameters of a gas chromatograph after a new column is installed in accordance with a new chromatographic method such that the retention times of all compounds match those defined in the original chromatographic method, without using tedious indices calibrations. In particular, this would simplify installation and validation of the new method chromatographic; reduce the cost of setting up methods; reduce errors associated with changes in the calibration; and provide for automation of the set up procedure in combination with electronic pneumatics control, or manual with mechanical control if necessary.

There is a need for a method for predictably translating a known chromatographic method to work with a column having different column parameters such that retention times obtained by the original column are predictably recast with no change in the order of elution.

Another object of the invention is to incorporate retention time locking into a gas chromatograph that automatically translates known methods to accommodate columns of diameters or lengths, as well as operational parameters that vary from a known chromatographic method, and yet maintain retention time locking. In particular, it is desirable to have the gas chromatograph automatically configure with new operating parameters such that the chromatographic output of the gas chromatograph with the new column and operating parameters is the same as with the original column and operating parameters.

It would be desirable and of considerable advantage to lock the retention times of the new column to match the retention times of the original column without numerous recalibrations, so as to provide an improvement in one or more of the following: substitution of any available column having the same stationary phase coating, the ability to provide for reoptimization and direct comparability to existing chromatographic methods, provide for a predictable improvement in analysis speed, capacity, improved troubleshooting and diagnostics, increased remote support ability, accuracy of quantification or resolution, and the identification of compounds.

SUMMARY OF THE INVENTION

The invention provides a method for adjusting operational parameters of a gas chromatograph, including column head pressure, to compensate for use of a column having column parameters that differ from the parameters expressed in a known chromatographic method, such that the retention times obtained with the column are matched to the retention times specified in the known chromatographic method.

In a first embodiment, the column parameters of a new column are ascertained and substituted into a set of equations that define flow through the new column. These equations are solved simultaneously to provide a set of new operating parameters. The gas chromatograph is then configured with the new operating parameters. Matching of the new column void time and the original column void time is confirmed by injecting a non-retained compound into the new column and measuring the void time. If no match is confirmed, the head pressure and the internal diameter of the original column are employed for calculating the actual length of the new column. From the calculated length, a new head pressure is determined that provides for matching the void time of the new column to that specified in the known chromatographic method. While matching the void times is usually enough to match retention times, further adjustment of the head pressure may be employed to match the retention times of the new column to the specified retention times. A standard is injected to confirm whether there is a match of retention times. If the retention times do not match, pressure versus retention time relationships established for one of a number of different target peaks can then be employed for calculating an adjustment to the column head pressure to lock onto the retention time match. Notwithstanding the above, locking of the retention time may be employed without first matching the void times.

The present invention may also be employed for translation and retention time matching of a known chromatographic method where the known chromatographic method is first translated into a new chromatographic method by ascertaining the column parameters of the new column and the carrier gas being used, substituting the new parameters into a set of equations that define flow through the column and retention as a function of phase ratio, and solving the equations simultaneously so as to provide a new set of operating parameters and retention times. The retention times may be either the same as the original, or may be exactly recast ("scaled") from the original retention times. A non-retained compound is injected into the gas chromatograph configured in accordance with the calculated operating parameters and the void time is measured. The head pressure is then adjusted either manually or automatically such that the void time of the new column is matched with the void time of the known column. Once matched, a standard is injected into the gas chromatograph and a determination is made as to whether the retention times of the new column and the retention times of the known column match. If they do not, then an adjustment to the head pressure is calculated as previously set forth that provides for locking of the retention time match.

Improved transferability of chromatographic methods is an advantage that is obtained from the use of this method.

Other aspects and advantages of the present invention will become apparent from the following detailed description, taken in conjunction with the accompanying drawings, illustrating by way of example the principles of the invention.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DESCRIPTION OF THE PREFERRED EMBODIMENT

The invention provides a method for translation of a known chromatographic method having a defined set of column and operating parameters into a new chromatographic method having a new set of column and operating parameters, wherein retention times defined in the new chromatographic method are matched to the retention times in the known chromatographic method.

Figure 4:
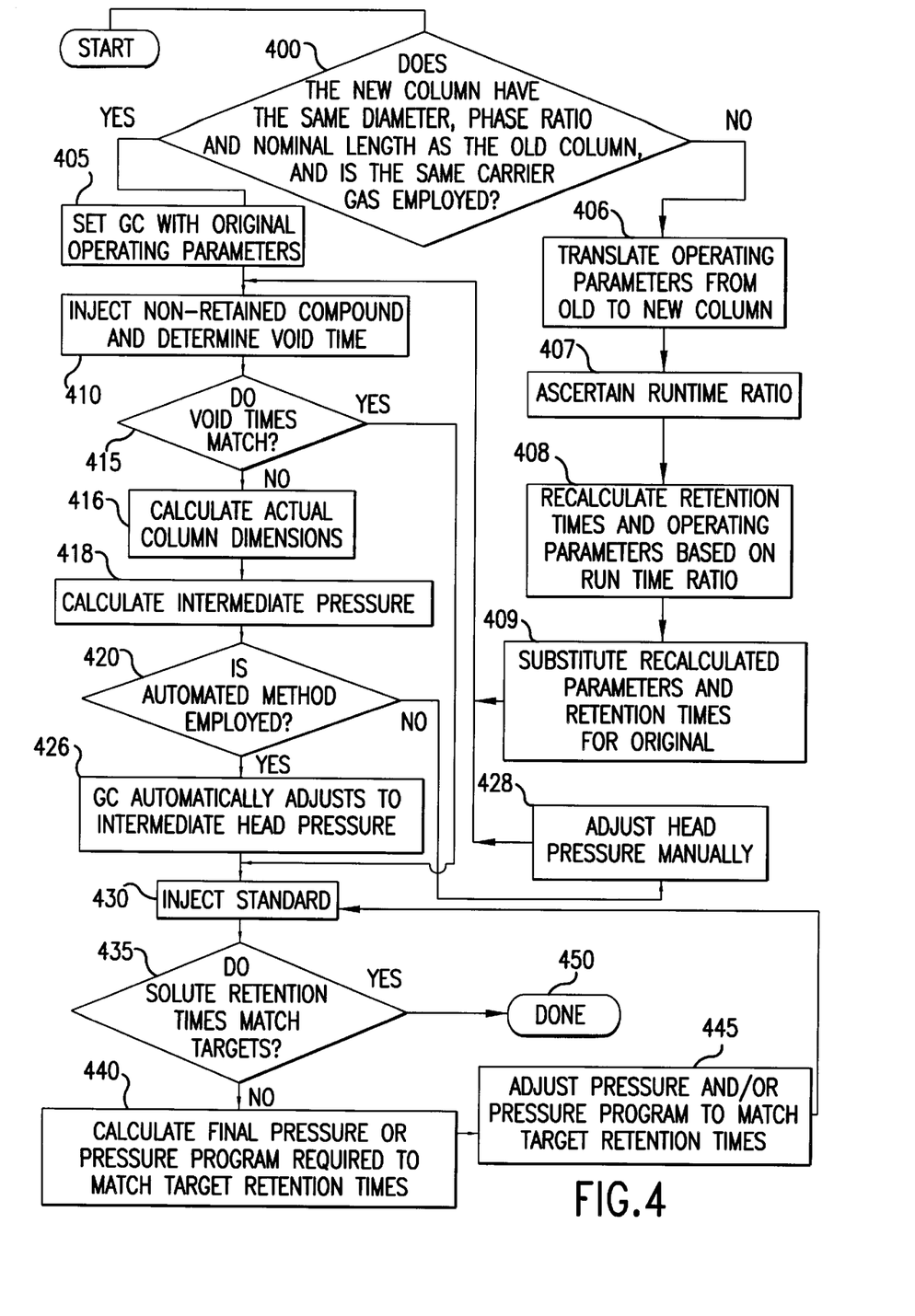
FIG. 4 is a flowchart of a method provided according to the invention.

FIG. 4 is a flowchart of the preferred embodiment of the invention. At step 400, the length, inside diameter and stationary phase ratio of a new column to be installed in a gas chromatograph are checked in addition to the carrier gas type employed. If all parameters except length are nominally the same as in the known method and the new column only has a relatively small difference in length (less than 25%), then no method translation is required and the gas chromatograph is configured with the original operating parameters specified in the known chromatographic method (step 405). If the new column has an inside diameter not within 20 percent of that of the old column, and/or a stationary phase ratios that is not nominally the same as that of the old column, or a different carrier gas is employed, then the known method must first be translated to compensate for such variations (step 406). If the difference in length between the new column and the old column is not within 50 percent, then method translation may be employed as one method for improving efficiency and speed. At step 407, the void time ratio (or runtime ratio) of the new column and the old column is ascertained such that new target retention times can be calculated (step 408). At step 410, the void time of the new column is ascertained by injecting a non-retained compound and timing how long the compound takes to traverse the column. The void-time thus ascertained is compared with the void time specified in the known method or the newly translated one (step 415). If the ascertained void time does not match, then the column head pressure must be adjusted. Automated pressure adjustment ("Yes" path of step 420) provides for calculating actual dimensions of the new column based on the ascertained void time (step 416), calculating a new pressure that will result in the desired void time (step 418), and automatically adjusting the head pressure to this pressure (step 426). Alternatively, the head pressure can be adjusted manually to the calculated pressure value (step 428) prior to injecting another non-retained compound (step 410), or an iterative approach could be employed for zeroing in on a new head pressure that provides for void time matching (step 428, 410, 415, 416, 418, and 420). Once the void time has been matched, target retention peaks often match. Improved matching may be possible if a standard is injected (step 430) and a determination is made as to whether the target retention times specified in the known method match the measured target retention times (step 435). If the target retention times do not adequately match, then the pressure change required to match the target retention times are calculated (step 440) and the pressure of the carrier gas is adjusted (step 445) such that when another standard is injected, the target retention times match. The process is completed when the measured and target retention times match (step 450).

Figure 5:
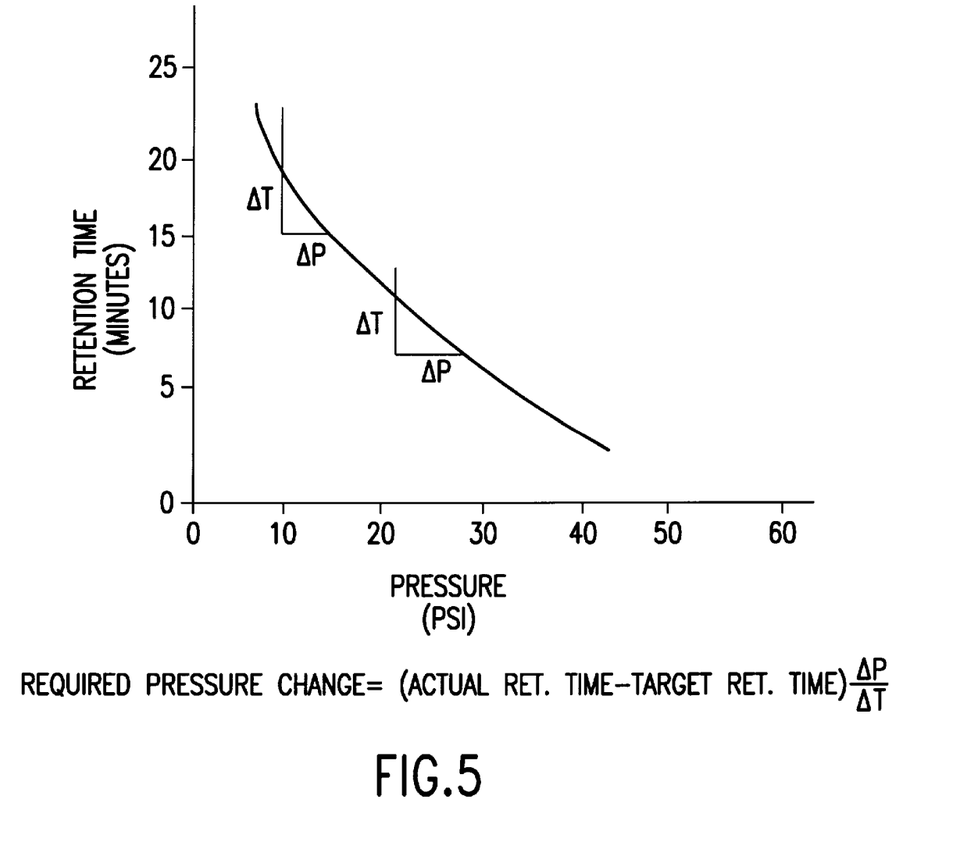
FIG. 5 illustrates the chromatographic output of a gas chromatograph of FIG. 1 in which the head pressure has been adjusted according to the method of FIG. 4 to lock void time and retention times.

Calculation step 440 further comprises the step of utilizing a baseline calibration table of the retention time for the target peak vs. column head pressure previously established by injecting the standard a series of times at different pressures. The change in retention time for the peak versus the change in pressure may be graphed (FIG. 5) to provide a vehicle for identifying the requisite adjustment in pressure required to match the retention times. In particular, it is possible to generate a single equation relating the pressure change required to change target retention times a known amount that suffices for all peaks. During locking, the difference between new and known retention times is determined such that the change in head pressure can be calculated. This method also provides for correcting small changes in phase ratio and for errors in the offset of the pressure measurement. Finally, this method can be done in combination with or independently of void time matching.

Additional fine tuning of retention times may be required if method translation is not used and the difference between the new column length and the original column is more than 25%, the column diameter differs from the original by more than 10%, the phase ratio differs by more than 10%, and/or if the carrier gas type is different. The additional fine tuning adjustment is accomplished by adjusting the head pressure during the run in accordance with a pressure program. The pressure program may be either linear, exponential or logarithmic, as determined by the skew in retention time differences from the beginning to the end of the run.

Figure 6A:
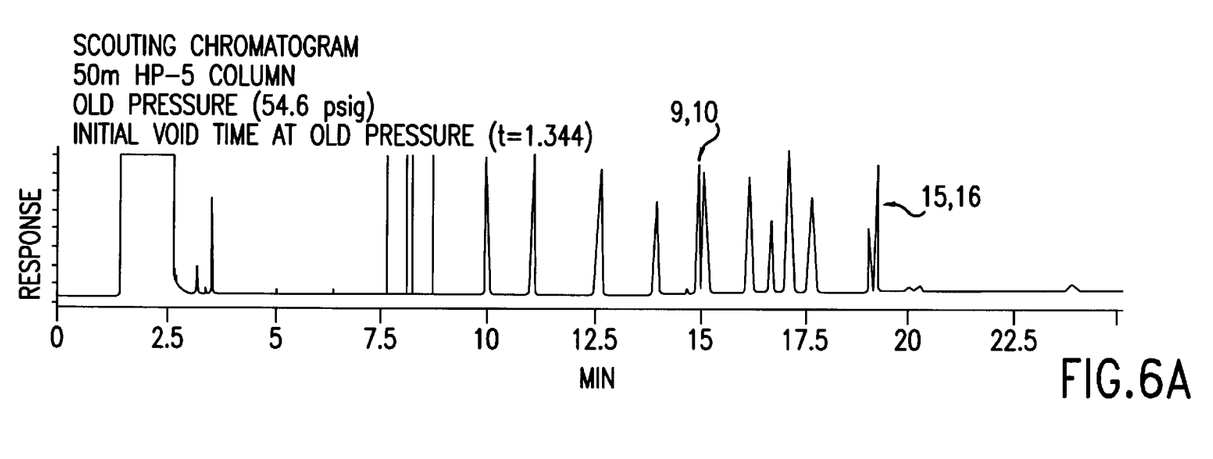
FIG. 6 collectively illustrates three chromatographic outputs, FIG. 6C being the target, FIG. 6A being a scouting run, and FIG. 6B illustrating retention time locking.
Figure 6B:
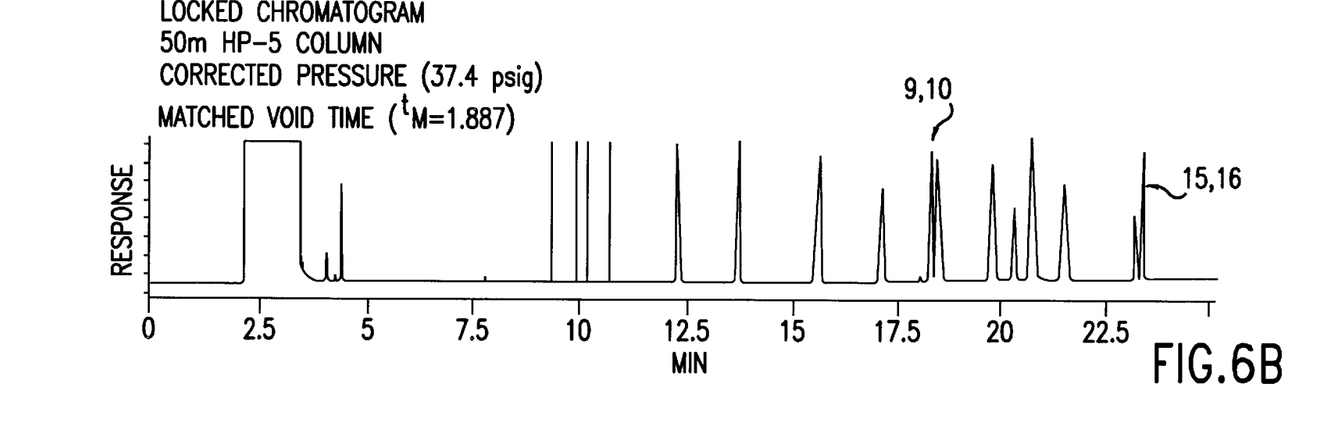
Figure 6C:
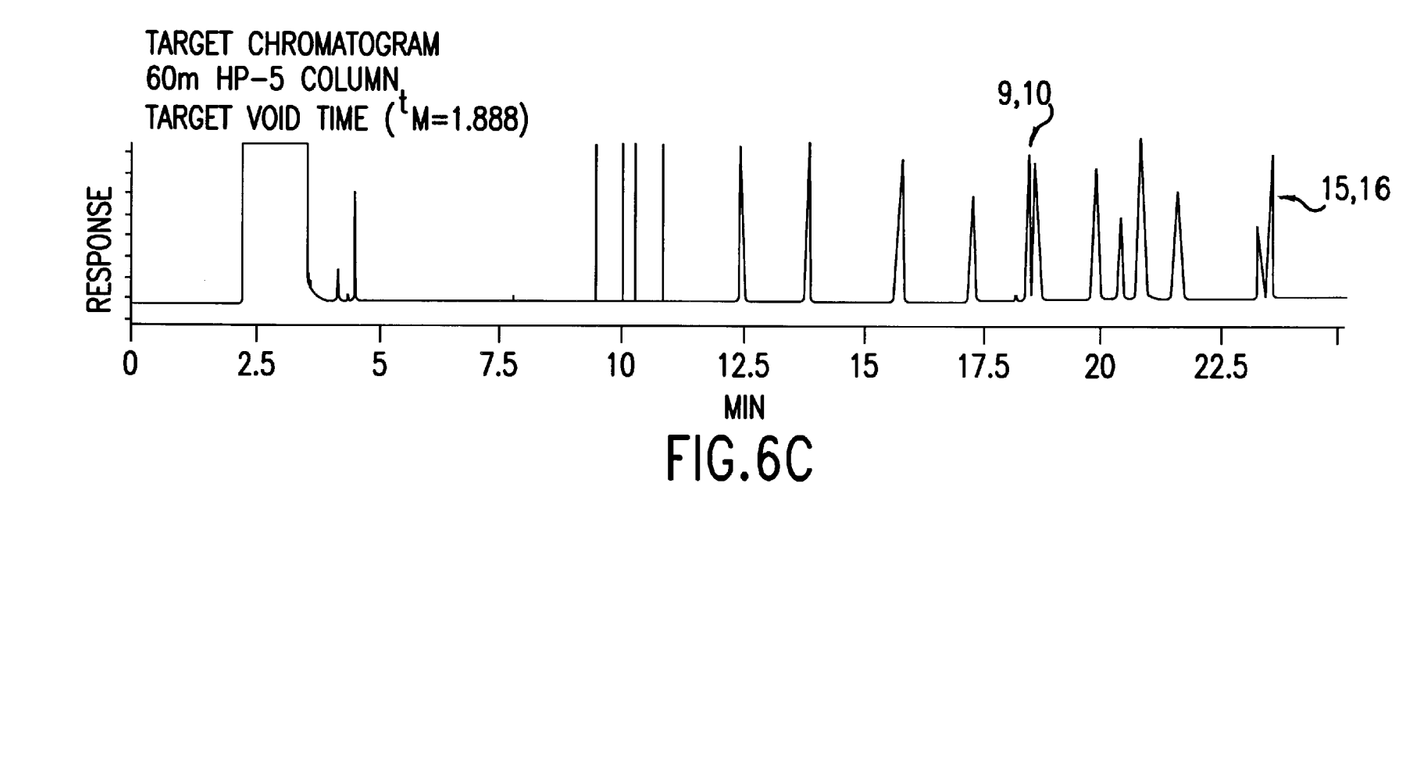

FIG. 6 illustrates the output of two different chromatographic columns. The chromatogram of FIG. 6C is a target chromatographic output of a 60 meter, 250 um inside diameter, 0.5 um HP-5 column that has been optimized for the separation of sixteen organochlorine pesticides. Two peak pairs (9,10 and 15,16) are resolution limited and represent the "target" to be reproduced. The length of the column was then reduced by ten meters and the invention was employed for matching the retention times. In particular, a standard was injected into the gas chromatograph to generate a "scouting chromatogram". As illustrated in FIG. 6A, the retention times of the scouting chromatograph are shorter than on the target chromatograph. FIG. 6B illustrates the results obtained when the column head pressure is adjusted to match void times and by fine tuning using a previously established relationship of change in retention times versus change in pressure.

Figure 7:
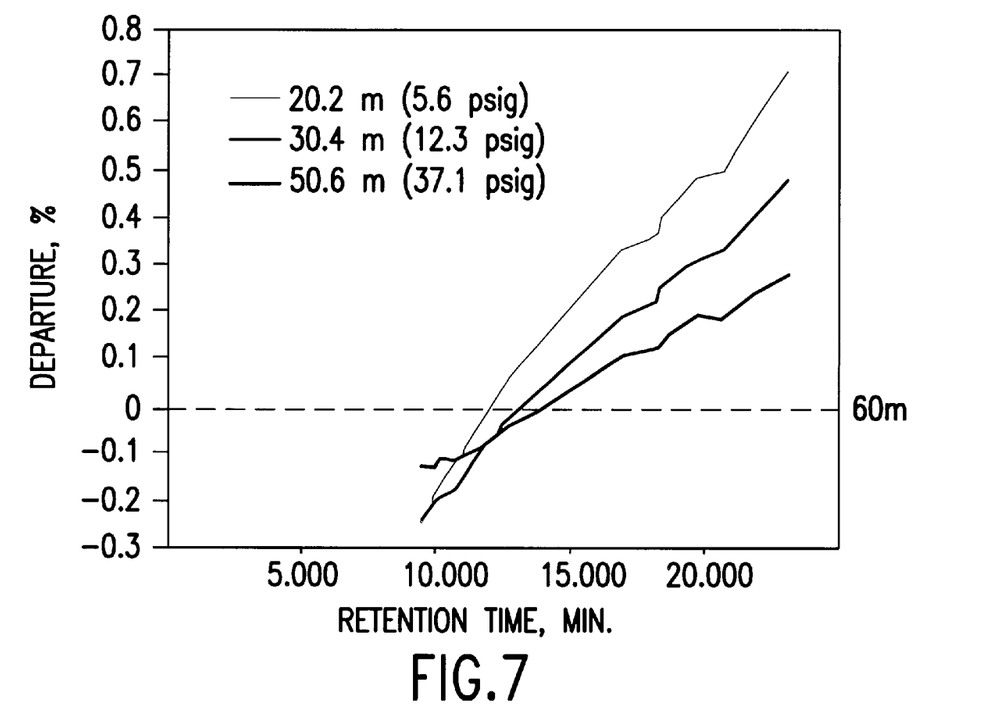
FIG. 7 illustrates the percent departure (%) of retention times from the target chromatogram for a known column that is 60 meters in length and for columns that are 50.6, 30.4, and 20.2 meters in length.

FIG. 7 illustrates the percent departure (%) of retention times from the target chromatogram for a column that is 60 meter in length and other columns that are 50.6, 30.4, and 20.2 meters in length. The skew in retention times, which becomes larger for larger differences in column lengths, can be corrected through the use of a pressure program (such as a constant linear velocity profile) in accordance with the invention.

Automated retention time locking advantageously provides for faster installation and checkout of new chromatographic systems, faster setup of methods to match a previous method, and the ability to use run time tables from another chromatographic method without modification/update. Additionally, the inventive method provides for faster, easier, more accurate interpretation of results including the ability to directly transfer and reproduce methods, including integration and time-table events, and to facilitate remote setup and diagnostics.

The invention may be employed for facilitating setup, increasing method accuracy and transferability of instrument methods because absolute target retention times are known. Thus, methods can be developed, documented, stored electronically and transferred within the instrument and/or across a modem for remote diagnostics. Documentation for regulatory compliance is also enhanced as everyone will be capable of matching the set same set of retention times, thus, simplifying documentation and validation.

The ability to conduct remote calibration of retention times facilitates trouble shooting and set up of distributed measurement devices after local instrument maintenance. Remote method updating could also include calibration and integration.

The ability to produce optimized chromatographic methods that specify exact retention times and run time events provides for the optimization of methods when current needs change (speed, resolution, capacity, column availability/type). In particular, the invention increases the portability of existing methods by leveraging time spent on the existing method by quickly yielding an accurate new method with predictable results, namely, it provides for the use of existing methods that are commonly available in the literature, regulations, or within an organization.

The dynamic range of the invention is illustrated when employed in combination with both a GC mass spectrometer detector and an Atomic Emission detector. The mass spectrometer works in a vacuum, retention times are typically less than for a traditional flame ionization detector when operating under identical chromatographic conditions. On the other hand, an atomic emission detector actually produces a positive gauge pressure and results in retention times that are typically greater than ordinary detectors. The invention provides for retention time matching regardless of the type of detector employed. Two different types of detectors provide for more precise compound identification using in combination with molecular, atomic, and/or other selective information.

While the invention has been described and illustrated with reference to specific embodiments in the area of retention time locking on a gas chromatograph, those skilled in the art will recognize that modification and variations may be made such that the invention is equally applicable to the field of remote analysis employing a chromatographic column that requires recalibration upon initial set up and/or after continued use, or other fields where exact replication of retention times is required or desired for improved usability, reliability, or maintenance. For example, the analysis of BTU content of natural gas at the point of use, or in portable safety monitoring devices.

What is claimed is:

1. A method for adjusting operating parameters of a gas chromatograph such that measured retention times of compounds are matched to prior retention times of the compounds, comprising the method steps of:

configuring the operating parameters in accordance with a known chromatographic method including a known column;

injecting a standard having a target compound a plurality of times, each time at one of a plurality of column head pressures to yield a plurality of retention times of the target compound, each at different column head pressures; and establishing a calibration curve for identifying the change in column head pressure required to effect a change in retention time sufficient to match the measured retention time of the target compound to the prior retention time of the target compound.

2. The method for adjusting operating parameters of a gas chromatograph as claimed in claim 1, further comprising the method steps of:

reinjecting the standard and ascertaining the measured retention time of the target compound; and calculating a final column head pressure from the measured retention time and the calibration curve such that the measured retention times for subsequent injections will match the prior retention times.

3. The method for adjusting operating parameters of a gas chromatograph as claimed in claim 2, further comprising, prior to the step of reinjecting, the method step of replacing the known column with a different column.

4. The method for adjusting operating parameters of a gas chromatograph as claimed in claim 2, wherein the method steps of reinjecting the standard and calculating a final column head pressure are performed using a different gas chromatograph.

5. The method for adjusting operating parameters of a gas chromatograph as claimed in claim 2, wherein the final column head pressure comprises a pressure program.

6. The method for adjusting operating parameters of a gas chromatograph as claimed in claim 2, wherein the method steps of reinjecting the standard and calculating a final column head pressure are performed periodically to recalibrate the gas chromatograph.

7. The method for adjusting operating parameters of a gas chromatograph as claimed in claim 1, further comprising the method steps of:

replacing the known column having known column parameters with an installed column having installed column parameters;

comparing the installed column parameters to the known column parameters to determine whether the inside diameters are within 20 percent, the stationary phase ratios are nominally the same, and the lengths are within 50 percent; and translating the known chromatographic method such that the measured retention times using the installed column are scaled to the prior retention times obtained using the known column, if any installed column parameter does not match the corresponding known column parameter within the specified tolerance.

8. The method for adjusting operating parameters of a gas chromatograph as claimed in claim 1, wherein the gas chromatograph includes a column, further comprising the method steps of:

replacing the known column having known column parameters with an installed column having installed column parameters;

comparing the installed column parameters to the known column parameters to determine whether the inside diameters are nominally the same, the stationary phase ratios are nominally the same, and the lengths are within 25 percent; and translating the known chromatographic method such that the measured retention times using the installed column are scaled to the prior retention times obtained using the known column, if any installed column parameter does not match the corresponding known column parameter within the specified tolerance.

9. The method for adjusting operating parameters of a gas chromatograph as claimed in claim 1, wherein the gas chromatograph includes a carrier gas, further comprising the method steps of:

changing the type of carrier gas; and translating the known chromatographic method such that the measured retention times using the changed carrier gas are scaled to the prior retention times using the prior carrier gas.

10. A method for adjusting operating parameters of a gas chromatograph such that measured retention times of compounds are matched to prior retention times of the compounds obtained using a known chromatographic method including known column parameters, comprising the steps of:

operating the gas chromatograph with an installed column having installed column parameters that differ in at least one of internal diameter, length, and phase ratio from the known column parameters;

configuring the operating parameters including a prior column head pressure in accordance with the known chromatographic method;

injecting a standard having a target compound into the gas chromatograph and ascertaining the measured retention time of the target compound; and calculating a final column head pressure from the measured retention time such that the measured retention times for subsequent injections will match the prior retention times.

11. The method for adjusting operating parameters of a gas chromatograph as claimed in claim 10, wherein the step of calculating a final column head pressure further comprises use of an established relationship of change in retention time versus change in column head pressure to determine the pressure change required to match retention times.

12. The method for adjusting operating parameters of a gas chromatograph as claimed in claim 10, wherein the method steps of configuring, injecting, and calculating are performed periodically to recalibrate the gas chromatograph.

13. The method for adjusting operating parameters of a gas chromatograph as claimed in claim 10, further comprising, prior to the step of configuring the operating parameters, the method steps of:

comparing the installed column parameters to the known column parameters to determine whether the inside diameters are within 20 percent, the stationary phase ratios are nominally the same, and the lengths are within 50 percent; and translating the known chromatographic method such that the measured retention times using the installed column are scaled to the prior retention times obtained using the known column, if any installed column parameter does not match the corresponding known column parameter within the specified tolerance.

14. The method for adjusting operating parameters of a gas chromatograph as claimed in claim 10, further comprising, prior to the step of configuring the operating parameters, the method steps of:

comparing the installed column parameters to the known column parameters to determine whether the inside diameters are nominally the same, the stationary phase ratios are nominally the same, and the lengths are within 25 percent; and translating the known chromatographic method such that the measured retention times using the installed column are scaled to the prior retention times obtained using the known column, if any installed column parameter does not match the corresponding known column parameter within the specified tolerance.

15. A method for adjusting operating parameters of a gas chromatograph such that measured retention times of compounds are matched to prior retention times of the compounds obtained using a known chromatographic method including a first carrier gas, comprising the method steps of:

translating the known chromatographic method to compensate for a change to a second carrier gas;

configuring the operating parameters including a prior column head pressure in accordance with the translated chromatographic method;

injecting a standard having a target compound into the gas chromatograph using the second carrier gas and ascertaining the measured retention time of the target compound; and calculating a final column head pressure from the measured retention time such that the measured retention times for subsequent injections match the prior retention times.

16. A method for adjusting operating parameters of a gas chromatograph such that measured retention times of compounds are matched to prior retention times of the compounds obtained using a known chromatographic method including a first column outlet pressure associated with a first detector type, comprising the method steps of:

operating the gas chromatograph at a second column outlet pressure associated with a second detector type;

configuring the operating parameters in accordance with the known chromatographic method;

injecting a standard having a target compound a plurality of times, each time at one of a plurality of column head pressures to yield a plurality of retention times of the target compound, each at different column head pressures; and establishing a calibration curve for identifying the change in column head pressure required to effect a change in retention time sufficient to match the measured retention time of the target compound using the second detector type to the prior retention time of the target compound obtained using the first detector type.

17. The method for adjusting operating parameters of a gas chromatograph as claimed in claim 16, further comprising the method steps of:

reinjecting the standard and ascertaining the measured retention time of the target compound; and calculating a final column head pressure from the measured retention time and the calibration curve such that the measured retention times for subsequent injections using the second detector type will match the prior retention times obtained using the first detector type.

18. A method for adjusting operating parameters of a gas chromatograph such that measured retention times of compounds are matched to prior retention times of the compounds, comprising the method steps of:

configuring the operating parameters including a column head pressure in accordance with a known chromatographic method including a specified void time and specified column parameters including nominal column dimensions;

injecting a non-retained compound into the gas chromatograph and determining an ascertained void time;

calculating actual column dimensions based on the ascertained void time; and calculating an adjusted column head pressure based on the actual column dimensions such that the ascertained void time for subsequent injections matches the specified void time.

19. The method for adjusting operating parameters of a gas chromatograph as claimed in claim 18, wherein the calculating steps are performed using known equations of flow through open tubes.

20. The method for adjusting operating parameters of a gas chromatograph as claimed in claim 18, further comprising the method step of installing a new column having new column parameters in the gas chromatograph.

21. The method for adjusting operating parameters of a gas chromatograph as claimed in claim 20, further comprising the method steps of:

comparing the installed column parameters to the known column parameters to determine whether the inside diameters are nominally the same, the stationary phase ratios are nominally the same, and the lengths are within 25 percent; and translating the known chromatographic method such that the measured retention times using the installed column are scaled to the prior retention times obtained using the known column, if any installed column parameter does not match the corresponding known column parameter within the specified tolerance.

22. The method for adjusting operating parameters of a gas chromatograph as claimed in claim 20, further comprising the method steps of:

comparing the installed column parameters to the known column parameters to determine whether the inside diameters are within 20 percent, the stationary phase ratios are nominally the same, and the lengths are within 50 percent; and translating the known chromatographic method such that the measured retention times using the installed column are scaled to the prior retention times obtained using the known column, if any installed column parameter does not match the corresponding known column parameter within the specified tolerance.

23. The method for adjusting operating parameters of a gas chromatograph as claimed in claim 18, further comprising the method steps of:

applying the adjusted column head pressure;

injecting a standard having a target compound into the gas chromatograph and ascertaining the measured retention time of the target compound; and calculating a final column head pressure from the measured retention time such that the measured retention times for subsequent injections match the prior retention times.

* * * * *